United States Patent [19]

Lin et al.

[11] Patent Number: 5,595,867

[45] Date of Patent: *Jan. 21, 1997

[54] METHOD AND KIT FOR ENZYMATICALLY DETERMINING THE PH OF A SPECIMEN

[75] Inventors: Cheng-I Lin, Cupertino; Yuh-Geng Tsay, Los Altos Hills, both of Calif.

[73] Assignee: Diagnostic Reagents, Inc., Sunnyvale, Calif.

[*] Notice: The term of this patent shall not extend beyond the expiration date of Pat. No. 5,567,581.

[21] Appl. No.: 452,171

[22] Filed: May 26, 1995

Related U.S. Application Data

[63] Continuation of Ser. No. 398,693, Mar. 6, 1995, abandoned.

[51] Int. Cl.$^6$ .................................................. C12Q 1/00

[52] U.S. Cl. .................................. 435/4; 435/10; 435/11; 435/12; 435/14; 435/28

[58] Field of Search .................................. 435/11, 14, 10, 435/12, 28, 4

[56] References Cited

U.S. PATENT DOCUMENTS 4,190,496  2/1980  Rubenstein .................................. 435/7

FOREIGN PATENT DOCUMENTS 1255934  9/1986  U.S.S.R. .

Primary Examiner—Carolyn Paden
Attorney, Agent, or Firm—William B. Walker

[57] ABSTRACT

The present invention concerns a method of enzymatically determining the pH of a specimen (e.g., a solution or a biological fluid) and a kit for conducting the method. The present method involves mixing (1) a specimen with (2) an enzyme and (3) one or more substrates for the enzyme in a buffered solution having a pH effective to provide a direct proportional relationship between the activity of the enzyme and the pH of the specimen; determining the activity of the enzyme; and correlating the activity of the enzyme to the pH of the specimen. Each of the sample, the enzyme, the substrate and the buffered solution is present in an amount effective to provide the direct proportional relationship between the activity of the enzyme and the pH of the specimen. The present kit contains an enzyme, one or more substrates for the enzyme present in an amount effective to determine the enzyme activity, and a buffered solution having a pH effective to provide a direct proportional relationship between the activity of the enzyme and the pH of the specimen. The present invention is particularly applicable to detecting adulteration of a urine specimen.

27 Claims, 2 Drawing Sheets

METHOD AND KIT FOR ENZYMATICALLY DETERMINING THE PH OF A SPECIMEN

This is a Continuation of application Ser. No. 08/398,693, filed on Mar. 6, 1995, now abandoned.

BACKGROUND OF THE INVENTION

1. Field of the Invention

The present invention concerns a method of enzymatically determining the pH of a specimen (e.g., a solution or a biological fluid) and a kit for conducting the method.

2. Discussion of the Background

Enzyme activities are generally known to be pH dependent. Typically, a graph showing the relationship of enzymatic activity (plotted along the ordinate) to pH (plotted along the abscissa) contains a bell-shaped curve (e.g., FIG. 1). Although such information is useful for predicting enzymatic activity as a function of pH (e.g., for determining optimum pH and maximizing enzymatic activity), the converse relationship does not necessarily exist; that is, one cannot conclusively determine the pH of a sample containing the enzyme from the enzyme activity information alone. A horizontal line corresponding to a given enzymatic activity intersects a bell-shaped curve such as that in FIG. 1 at two or more points. As a result, from a given set of test conditions, more than one pH value may correspond to a given enzymatic activity.

Drug testing is becoming an increasingly important tool for improving safety, security and productivity in a broad range of industries and commercial activities (e.g., transportation, medicine, defense, government, etc.). A number of Federal guidelines exist for implementing and conducting drug testing (see, for example, Executive Order No. 12564, "Mandatory Guidelines for Federal Workplace Drug Testing Programs," *Federal Register*, Sep. 15, 1988).

The integrity and proper identity of specimens collected are critical for success in drug testing. For example, a urine-based drug testing program normally involves the steps of (1) specimen collection, (2) an initial-immunoassay based screening test (3) confirmation testing based on gas chromatography/mass spectrometry (GC/MS), and (4) the distribution of test results. Many drug users attempt to evade drug detection by adulterating the specimen. Such adulteration is intended to produce a false negative test result during initial immunoassay screening.

Common adulteration methods include dilution with water, substitution of a drug-free liquid, and addition of household materials or chemicals (e.g., vinegar, baking soda, table salt, lye [e.g., DRANO®], detergent, or a substance containing glutaraldehyde such as URINE-AID, etc.). A drug user may also attempt alter his or her urinary pH (i.e., urinary acidity or alkalinity) to facilitate faster elimination of certain drugs or drug metabolites through metabolic processes. This latter technique may be applicable to elimination of alkaloids, amphetamines and phencyclidine, for example.

A number of methods may detect or deter urine adulteration, including temperature measurement, direct urine pH measurement, determination of the specific gravity of the sample and/or determination of the presence and/or concentration of creatinine. "Normal" urine should have a temperature of 32.5°–37.7° C. (90.5°–99.8° F.), a pH of 5–8, a specific gravity of 1.003–1.030 and a creatinine concentration of 0.8–1.4 mg/dL. If any of these parameters are outside the specified ranges, one has reason to suspect the urine specimen has been adulterated.

Prior to the present invention, urine pH measurement has been determined by use of pH paper or by an endpoint colorimetric pH measurement method (e.g., the pH PERFECT® drug testing adulteration testing kit, available from Chimera Research & Chemical, Inc., Seminole, Fla.). However, methods using pH paper are slow, subjective and cannot be adapted to existing clinical chemistry analyzers for high-volume urine screening applications. Colorimetric methods typically suffer from a lack of an indicator which is suitable for applications over a broad pH range (i.e., pH 2–12).

As a result, a need exists for a simpler, more accurate method of determining the pH of a specimen (e.g., a solution or a biological fluid) which may be more applicable for high volume screening (e.g., urine testing), a more direct method of testing an adulterated specimen through pH measurement, and for a test kit for conducting such methods.

SUMMARY OF THE INVENTION

Accordingly, one object of the present invention is to provide a novel method for enzymatically determining the pH of a fluid which can be used for accurate and conclusive determination of the pH of a specimen.

A further object of the present invention is to provide a novel method for enzymatically determining the pH of a specimen which is simple to carry out and which is applicable to high volume screening (e.g., urine testing).

A further object of the present invention is to provide a kit for conducting the present method.

These and other objects of the present invention, which will be readily understood in the context of the following detailed description of the preferred embodiments, have been provided by:

a method of enzymatically determining the pH of a specimen, comprising (a) mixing in a buffered solution (i) a sample of said specimen with (ii) an enzyme having an activity and (iii) a one or more substrates for said enzyme, said buffered solution having a pH effective to provide a direct proportional relationship between said activity of said enzyme and the pH of said specimen, wherein each of said sample, said enzyme, said substrate and said buffered solution is present in an amount effective to provide said direct proportional relationship between said activity of said enzyme and the pH of said specimen, (b) determining said activity of said enzyme, and (c) correlating said activity of said enzyme to the pH of the specimen; and a kit for conducting the method.

BRIEF DESCRIPTION OF THE DRAWINGS

A more complete appreciation of the present invention and many of the attendant advantages thereof will be readily obtained as the same become better understood by reference to the following detailed description of the preferred embodiments when considered in connection with the accompanying drawings, wherein.

DESCRIPTION OF THE PREFERRED EMBODIMENTS

Figure 1:
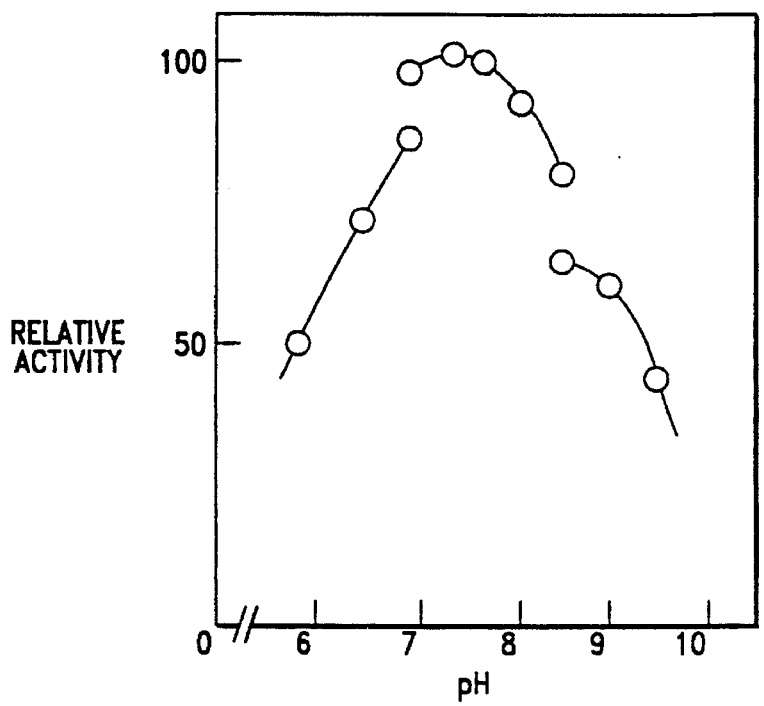
FIG. 1 is a graph depicting the relationship between enzyme activity (ordinate) and pH (abscissa) for glucose-6-phosphate dehydrogenase (G6PDH)

In the context of the present application, a "specimen" refers to a substance which will be, which is or which has been subjected to analysis. A "specimen" may refer to a solution (the contents of which may be known or unknown, or which may be aqueous or non-aqueous), a biological fluid (such as urine, whole blood, blood serum, blood plasma, saliva, etc), a tissue homogenate (e.g., homogenized lung, heart, brain, liver, kidney, etc.) or a solution thereof (which may be filtered prior to analysis), or to a solid or lyophilized sample (a solution of which may be prepared prior to testing). In the context of the present application, a "specimen" preferably refers to an aqueous or water-containing solution (and more preferably, to a collected biological fluid) for which one or more methods of determining the pH exist.

The present invention is applicable to any enzyme, any substrate(s) therefor, and any buffer, as long as a direct proportional relationship between the pH of a specimen and enzyme activity can be established. A direct proportional relationship between the pH of a specimen and enzyme activity can be obtained by controlling the pH of the buffer and the volumes of the sample of the specimen being tested and the buffered solution. A "direct proportional" relationship is one which may comply with the following formula:

$$y = a_0 x^n + a_1 x^{n-1} + \ldots a_{n-1} x + a_n$$

where y is the pH of the specimen; $a_0, a_1 \ldots a_{n-1}$ and $a_n$ represent a series of constants; and x represents the enzymatic activity. Preferably, the direct proportional relationship between the specimen pH and the enzyme activity is a linear relationship (i.e., where $y = a_{n-1} x + a_n$).

Furthermore, the present invention can be conducted using any commercially available equipment conventionally used for determining and/or measuring enzyme activities, but a conventional clinical chemistry analyzer (e.g., HITACHI 704, 717 737, 747; OLYMPUS AU800, AU5000, AU5200 REPLY; IL MONARCH; Roche COBAS MIRA, COBAS FARA; Beckman SYNCHRON CX; Corning EXPRESS; etc.) is the preferred apparatus for analyzing enzyme activity.

The enzyme and substrate(s) are typically present in an amount effective to determine enzyme activity. Amounts of enzyme and substrate and methods for determining enzyme activity are known for a very large number of enzyme-substrate combinations. In the present invention, enzyme activity can be measured or determined in accordance with conventional methods.

In the present method of enzymatically determining the pH of a specimen, one may first select an enzyme and one or more appropriate corresponding substrate(s) for determining the activity of the enzyme. For example, if G6PDH is selected as the enzyme, glucose-6-phosphate (G6P) and nicotinamide adenine dinucleotide (NAD) are selected as substrates. The buffer for determining the pH of the specimen may be selected thereafter on the basis of a graph plotting pH against enzyme activity for the selected enzyme and substrate(s).

The pH of the buffered solution in the present method of determining the pH of a specimen is selected such that it falls in the middle of a pH range in which a roughly linear relationship to enzyme activity exists, but in which the enzyme activities at the ends of the range are widely disparate. For example, FIG. 1 shows the relationship between relative enzyme activity (ordinate) and pH of the enzyme reaction solution (abscissa) for glucose-6-phosphate dehydrogenase (G6PDH). The activity of G6PDH is roughly linear in the pH range from 5.7 to 6.8. This pH range also provides an acceptably disparate range of relative activities at the endpoints (i.e., a relative activity of about 50% at pH 5.7 and about 85% at pH 6.8). However, for G6PDH, the pH range of from 7.5 to 9.5 also provides a roughly linear enzyme activity relationship and a suitably disparate range of relative enzyme activities. Any pH in a suitable range may be selected for the buffered solution to be used in accordance with the present invention. However, a pH in the middle (e.g., $M \pm ((0.5)(b-a))$, where "M" is the midpoint, "b" is the higher endpoint and "a" is the lower endpoint) of a suitable pH range for a particular enzyme-substrate combination is preferred.

A great number of enzymes and corresponding substrates therefor are known. Enzymes and corresponding substrates which can be used in the present invention are disclosed in U.S. Pat. No. 4,190,496 (col. 32, line 33 through col. 38, line 44, incorporated herein by reference) and in the Toyobo Manual, Section I, Enzymes, pages 1–162, which include information regarding the following enzymes:

| I.U.B. No. | Enzyme |
|---|---|
| 3.1.1.7 | Acetylcholinesterase |
| 3.1.3.2 | Acid Phosphatase, wheat germ |
| 1.1.1.1 | Alcohol Dehydrogenase, liver |
| 1.1.1.1 | Alcohol Dehydrogenase, yeast |
| 4.1.2.13 | Aldolase |
| 3.1.3.1 | Alkaline Phosphatase, chicken intestine |
| 3.1.3.1 | Alkaline Phosphatase, E. coli |
| 1.4.3.3 | D-Amino Acid Oxidase |
| 1.4.3.2 | L-Amino Acid Oxidase |
| 3.2.1.1 | α-Amylase |
| 3.2.1.2 | β-Amylase |
| 3.5.3.1 | Arginase |
| 4.1.1.9 | Arginine Decarboxylase |
| 3.5.1.1 | Asparaginase |
| 4.1.1.11 | Aspartic Acid Decarboxylase (See Glutamic Decarboxylase) |
| 3.1.1.8 | Butyrylcholinesterase |
| 4.2.1.1 | Carbonic Anhydrase |
| 3.4.2.1 | Carboxypeptidase A |
| 3.4.2.2 | Carboxypeptidase B |
| 1.11.1.6 | Catalase |
| 3.2.1.4 | Cellulase |
| 3.1.1.7 | Cholinesterase, Acetyl |
| 3.1.1.8 | Cholinesterase, Butyryl |
| 3.4.4.11 | Chymopapain |
| 3.4.4.5 | Chymotrypsin |
| 3.4.4.5 | Chymotrypsinogen |
| 3.4.4.19 | Collagenase |
| 2.7.8.2 | Creatine Kinase |
| 1.1.2.3 | Cytochrome $b_2$ |
| 4.1.1– | Decarboxylases |
| 3.1.4.5 | Deoxyribonuclease |
| 3.1.4.6 | Deoxyribonuclease II |
| 3.2.1.11 | Dextranase |
| 1.6.99– | Diaphorase |
| 3.2.2.5 | DPNase |
| 3.4.4.7 | Elastase |
| 3.2.1.21 | Emulsin |
| 2.7.–.– | Firefly Extract |
| 3.1.3.11 | Fructose 1,6-Diphosphatase |
| 1.1.3.9 | Galactose Oxidase |
| 3.2.1.23 | β-Galactosidase |
| 1.1.3.4 | Glucose Oxidase |
| 1.1.1.49 | Glucose-6-Phosphate Dehydrogenase |

-continued

| I.U.B. No. | Enzyme |
|---|---|
| 3.2.1.21 | β-Glucosidase |
| 3.2.1.31 | β-Glucuronidase, beef liver |
| 3.2.2.31 | β-Glucuronidase, E. coli |
| 4.1.1.15 | Glutamic Acid Decarboxylase |
| 2.6.1.1 | Glutamic Oxaloacetic Transaminase |
| 3.5.1.2 | Glutaminase |
| 1.2.1.12 | Glyceraldehyde Phosphate Dehydrogenase |
| 1.1.1.6 | Glycerol Dehydrogenase |
| 4.3.1.3 | Histidase |
| 3.2.1.35 | Hyaluronidase |
| 1.1.1.50 | Hydroxysteroid Dehydrogenase |
| 1.1.1.51 | Hydroxysteroid Dehydrogenase *Pseudomonas testosteroni* |
| 3.6.1.1 | Inorganic Pyrophosphatase |
| 3.2.1.23 | Lactase (See β-Galactosidase) |
| 1.1.1.27 | Lactase Dehydrogenase, rabbit muscle |
| 1.1.1.27 | Lactase Dehydrogenase, beef heart |
| 1.1.1.27 | Lactase Dehydrogenase, isozymes |
| 1.1.2.3 | L-Lactate Dehydrogenase |
| 3.1.4.3 | Lecithinase C |
| 3.4.1.1 | Leucine Aminopeptidase |
| 3.1.3.2 | Lipase, wheat germ (Acid Phosphatase) |
| 3.1.1.3 | Lipase, pancreatic |
| 1.99.2.1 | Lipoxidase |
| 1.2.-.- | Luciferase |
| 2.7.-.- | Luciferase, firefly |
| 4.1.1.18 | Lysine Decarboxylase |
| 3.2.1.17 | Lysozyme |
| 1.1.1.37 | Malate Dehydrogenase |
| 3.4.4.10 | Mercuripapain |
| 3.2.1.18 | Neuraminidase |
| 3.1.4.7 | Nuclease, *Staph. aureus* |
| 4.1.1.2 | Oxalate Decarboxylase |
| 3.4.4.10 | Papain |
| 3.1.1.11 | Pectin Methyl Esterase |
| 3.4.4.1 | Pepsin |
| 3.4.4.1 | Pepsinogen |
| 1.11.1.7 | Peroxidase |
| 3.1.3.2 | Acid Phosphatase |
| 3.1.3.1 | Alkaline Phosphatase, chicken intestine |
| 3.1.3.1 | Alkaline Phosphatase, *E. coli* |
| 3.1.4.1 | Phosphodiesterase I, venom |
| 3.1.4.1 | Phosphodiesterase II, spleen |
| 3.1.4.3 | Phospholipase C |
| 2.4.1.1 | Phosphorylase a |
| 2.4.1.1 | Phosphorylase b |
| 2.7.7.8 | Polynucleotide Phosphorylase |
| 1.10.3.1 | Polyphenol Oxidase |
| 3.4.4.4, 3.4.4.5 | Protease |
| 2.7.1.40 | Pyruvate Kinase |
| 2.7.7.16 | Ribonuclease A |
| 2.7.7.16 | Ribonuclease B |
| 2.7.7.26 | Ribonuclease $T_1$ |
| 2.6.1.1 | Transaminase |
| 3.4.4.4 | Trypsin |
| 3.4.4.4 | Trypsinogen |
| 1.10.3.1 | Tyrosinase |
| 4.1.1.25 | Tyrosine Decarboxylase |
| 4.1.1.25 | Tyrosine Decarboxylase-Apoenzyme |
| 3.5.1.5 | Urease, *B. Pasteurii* |
| 3.5.1.5 | Urease, Jack Bean Meal |
| 1.7.3.3 | Uricase |
| 1.2.3.2 | Xanthine Oxidase |

In particular, the following table provides specific examples of enzymes, their corresponding substrate(s), suitable pH ranges for the buffered solution in which their activity is measured in accordance with the present invention, and particularly preferred exemplary pH's:

TABLE

| Enzyme | Substrate(s) | pH Ranges | Exemplary pH's |
|---|---|---|---|
| Cholesterol oxidase | cholesterol | 4.0–6.0 | 5.0 |
| | (oxygen)* | 7.0–9.0 | 8.0 |
| β-galactosidase | β-D-galactoside | 5.0–6.5 | 5.8 |
| | (water)* | 7.5–9.5 | 8.5 |
| Glucose-6-phosphate dehydrogenase | D-glucose-6-phosphate, $NAD^+$ or $NADP^+$ | 5.0–7.0 | 6.5 |
| | | 7.5–9.5 | 8.5 |
| Glucose oxidase | glucose | 3.0–4.5 | 3.5 |
| | (oxygen, water) | 7.0–10.0 | 8.0 |
| Horseradish peroxidase | (donor)[1] | 4.0–6.0 | 5.0 |
| | $H_2O_2$ | 6.8–8.0 | 7.5 |
| Uricase | uric acid | 6.0–8.0 | 7.0 |
| | (oxygen, water) | 9.0–11.0 | 9.5 |
| Urease | urea | 4.0–6.0 | 5.0–5.5 |
| | (water) | 6.0–10.0 | 8.0–8.5 |

*: additional substrate(s) which are not necessarily added to the enzyme activity test solution
[1]: "Donor" refers to a compound oxidizable by horseradish peroxidase After a suitable pH for the buffered solution is selected, an appropriate buffer system for providing the desired pH and appropriate volumes of specimen sample and of buffered solution are selected. The system may then be calibrated with a variety of specimens, each having a known pH. The amounts of buffer and specimen may be varied, if necessary, and the range of known pH specimens tested, until a direct proportional relationship between pH of the specimen and enzyme activity is obtained. Although a non-linear relationship between specimen pH and enzyme activity is suitable, a linear relationship is preferred. As a result, the selections of enzyme, buffer, and relative proportions by volume of buffered solution to specimen sample are determined empirically, in a manner which results in selection of an effective amount of buffered solution having an effective pH to provide a direct proportional (preferably linear) relationship between enzyme activity and pH of a specimen.

To calibrate the system and determine whether the desired relationship exists, sample solutions of known pH are prepared. The previously selected enzyme and substrate may be dissolved into separate solutions, at least one of which is the buffered solution having the selected pH. The enzyme and substrate solutions are then reacted in the presence of the sample solution of known pH, for example by independently combining each of the sample solutions with one of (a) the enzyme solution or (b) the substrate solution prior to reaction of the enzyme solution with the substrate solution.

For example, at least three solutions of known pH in the range of from 2 to 12 should be tested during calibration. More particularly, the solutions of known pH comprise a sample of low pH (e.g., pH=2.0), a sample of neutral pH (e.g., pH=7.0) and a sample of relatively high pH (e.g., pH=12.0). However, the greater the number of sample solutions of known pH tested, the greater the accuracy in determining the relationship between specimen pH and enzyme activity. More preferably, a calibration employs at least five solutions of known pH (e.g., in addition to the three mentioned above, a fourth solution having a moderately low pH (e.g., pH=4.0), and a fifth solution having a moderately high pH (e.g., pH=10.0)). An even more preferred embodiment employs at least seven sample solutions of known pH (e.g., in addition to the five mentioned above, a sixth solution having a mildly acidic pH (e.g., pH=5.5 and a seventh solution having a mildly alkaline pH (e.g., pH=8.5)), and a most preferred embodiment employs a series of sample solutions having successive pH's of 2.0, 3.0, 4.0, 5.0, 6.0, 7.0, 8.0, 9.0, 10.0, 11.0 and 12.0.

A linear relationship between enzyme activity and sample pH can be observed under different standard conditions. For example, a higher concentration of buffer reagents in the buffered solution may permit use of a greater volume of specimen sample relative to the total volume of buffered solution. Thus, for a given enzyme/substrate combination, the ratio of the volumes of sample solution to buffered solution may vary, depending on the concentration of the buffer.

After an appropriate ratio of the volume of sample solution to the volume of buffered solution is determined for a selected test system, one can confirm a linear relationship between the pH of a sample solution and enzymatic activity by testing the pH as determined by the present enzymatic method against pH as determined by direct measurement with a properly calibrated pH meter. A correlation coefficient ($r^2$) of at least 0.90, and preferably at least 0.99, indicates that the enzymatic method of determining pH is acceptable and sufficiently accurate for use in determining pH or in analyzing a specimen (which may be either adulterated or non-adulterated) for drug testing.

Any buffer providing the desired pH which does not interfere the measurement of enzyme activity is suitable for use in the present invention. However, more specifically, a conventional acetate buffer can be used to provide a pH of 6.0 or less; a conventional phosphate buffer can be used to provide a pH of from 5.5 to 9.5; a carbonate-bicarbonate buffer (e.g., $K_2CO_3$—$NaHCO_3$) buffer can be used to provide a pH of from 8.5 to 11.0; a conventional Britton-Robinson buffer can be used to provide a pH of from 5.0 to 9.0; a conventional Veronal-sodium acetate-HCl buffer can be used to provide a pH of from 3.0 to 9.0; a TRIS-HCl buffer can be used to provide a pH of from 6.8 to 8.5; a conventional glycine-NaOH buffer can be used to provide a pH of from 8.5 to 9.5; a conventional borate buffer can be used to provide a pH of from 8.0 to 11.0; a conventional EDTA buffer can provide a pH of about 8.5; etc.

In the present invention, the enzyme and substrate may be dissolved in one or more buffers providing the selected pH prior to their subsequent combination with the specimen. The enzyme, substrate and sample may be mixed in the buffered solution in any order, as long as the enzyme activity can be appropriately determined. For example, the enzyme and substrate may be mixed in a dry form, and separately, the buffered solution may be combined with the specimen prior to mixing with the dry enzyme and substrate. Alternatively, the dry enzyme and substrate may be further mixed with dry buffer reagents which provide the desired pH for the buffered solution. In this embodiment, the sample of the specimen may be diluted with an appropriate amount of water (which may be distilled and/or deionized water) prior to mixing with the dry enzyme, substrate(s) and buffer reagents.

Alternatively, as described above, separate solutions of enzyme and substrate(s), at least one of which comprises the buffered solution, may be prepared. The specimen may be added to one of the enzyme or substrate solutions before determination of the enzyme activity. In a further alternative embodiment, the sample and the solutions of enzyme and substrate (at least one of which is the buffered solution) may be combined simultaneously prior to determining the enzyme activity.

Although the enzyme, substrate(s), buffer, pH, relative proportions by volume of specimen to buffered solution and other conditions are determined empirically in accordance with the procedures described above, suitable conditions for the present method of enzymatically determining the pH of a specimen may include the following:

Concentration of enzyme: from 0.01 to 10 µg/mL

Concentration of substrate(s): sufficient to provide from 1 to 100 Km (Michaelis constant), preferably from 2 to 10 Km Concentration of buffer reagents: from 1 to 100 µmol/mL (1–100 mM), preferably 10 to 50 mM Ratio by volume of specimen to buffered solution: from 1:3 to 1:50, preferably from 1:5 to 1:25 and more preferably from 1:10 to 1:15

Temperature: within the range suggested for determining activity for the selected enzyme (e.g., from 15° to 40° C., preferably from 20° to 38° C.)

In one embodiment of the present method of enzymatically determining the pH of a specimen, the enzyme G6PDH, substrates therefor (G6P and NAD) and a pH of 6.5 for the buffered solution are selected. Accordingly, an amount of G6PDH effective to determine the enzyme activity (e.g.,.0.5 µg/mL) is dissolved in a pH 6.5 buffered solution (e.g., 125 microliters of 50 mM Tris, but any concentration in the range of 30–100 mM is believed to be effective). A solution of the substrates providing effective concentrations to determine enzyme activity is separately prepared (e.g., 8 mM of G6P and 5 mM of NAD at, for example, pH 5.2 in the absence of buffer). In this case, 125 microliters of each of the enzyme and the substrate solutions provides the desired relationship for a sample volume of 20 microliters.

In a further embodiment, the present method can be applied to detection of an adulterated urine specimen. Thus, the present invention also concerns a method of enzymatically detecting adulteration of a urine specimen, comprising (a) mixing in a buffered solution (i) a sample of the urine specimen with (ii) an enzyme having an activity and (iii) a one or more substrates for the enzyme, the buffered solution having a pH effective to provide a direct proportional relationship between the activity of the enzyme and the pH of the urine specimen, wherein each of the sample, the enzyme, the substrate and the buffered solution is present in an amount effective to provide the direct proportional relationship between the activity of the enzyme and the pH of the urine specimen, (b) determining the activity of the enzyme, (c) correlating the activity of the enzyme to the pH of the urine specimen, wherein a pH of less than 5 or greater than 8 is a positive indication of adulteration of the urine specimen.

The present invention also concerns a kit for conducting a method of enzymatically determining the pH of a specimen, comprising (a) an enzyme having an activity, (b) one or more corresponding substrates for the enzyme and (c) a buffered solution or reagents therefor providing a pH effective to provide a direct proportional relationship between the activity of the enzyme and the pH of the specimen. The enzyme and substrate(s) are present in amounts effective to measure the enzyme activity.

After determining appropriate amounts of enzyme, substrate(s) and buffer in accordance with the procedure described above, kits can be prepared which containing appropriate unit packages or vials of the components. For example, in the determination of pH using G6PDH, 125 μl of a 1 μg/mL solution of G6PDH in 50 mM Tris buffer (pH 6.5) and 125 μL of G6P (8 mM) and NAD (5 mM) in 1 mM Tris buffer (pH 5.2) provide a linear relationship between G6PDH enzyme activity and pH of a sample solution when 20 μL of sample solution are used. Thus, for a kit designed to conduct the present method on a total volume scale of from 10 μL to 1 mL, the present kit may contain (a) from 0.01 to 10 μg of dry enzyme, (b) from 0.05 to 100 mmol of dry substrate(s), and (c) dry buffering agents or a buffered solution effectively providing a buffer concentration of from 10 to 50 mM, as long as the relationship between enzyme activity and pH of the specimen being tested maintains a direct proportional relationship.

Alternatively, the present kit for conducting the present method of enzymatically determining the pH of a specimen may comprise (1) a buffered solution of an enzyme, the pH of the buffered solution and the concentrations of (i) the enzyme and (ii) the buffer reagents each being effective to provide a direct proportional relationship between enzyme activity and pH of the specimen, and (2) a solution of substrate(s) for the enzyme in a concentration effective to determine and/or measure enzymatic activity.

The present kit may also include appropriate labware for conducting the method, such as multi-well plates or cuvettes, which may be adherent (polystyrene) or non-adherent (polypropylene or Teflon®), which may be sealed and/or which may further contain dry enzyme, substrate(s), buffer reagents and/or buffer solution; one or more appropriately-sized micropipettes or microsyringes for transferring solutions; and/or appropriate indicator(s) for analyzing enzyme activity, as are known in the art.

In a further embodiment, the present kit may comprise (d) an indicator which visually displays either pH or enzyme activity, and/or (e) a reference chart which correlates the enzymatic activity to a positive indication of adulteration, a negative indication of adulteration, or both positive and negative indications of adulteration. For example, a reference chart may comprise the calibration curve for a particular enzyme/substrate/buffer system (in particular proportions). Alternatively, the reference chart may merely indicate the enzyme activities which correspond to a pH of 5 or a pH of 8. In such cases, an enzyme activity below that corresponding to a pH of 5 or above that corresponding to a pH of 8 determined on a urine specimen would be a positive indication of adulteration, and an enzyme activity between those corresponding to a pH of 5 and a pH of 8 would be a negative indication of adulteration by modifying the pH of the specimen.

Other features of the present invention will become apparent in the course of the following descriptions of exemplary embodiments which are given for illustration of the invention, and are not intended to be limiting thereof.

EXAMPLES

Example 1

Figure 2:
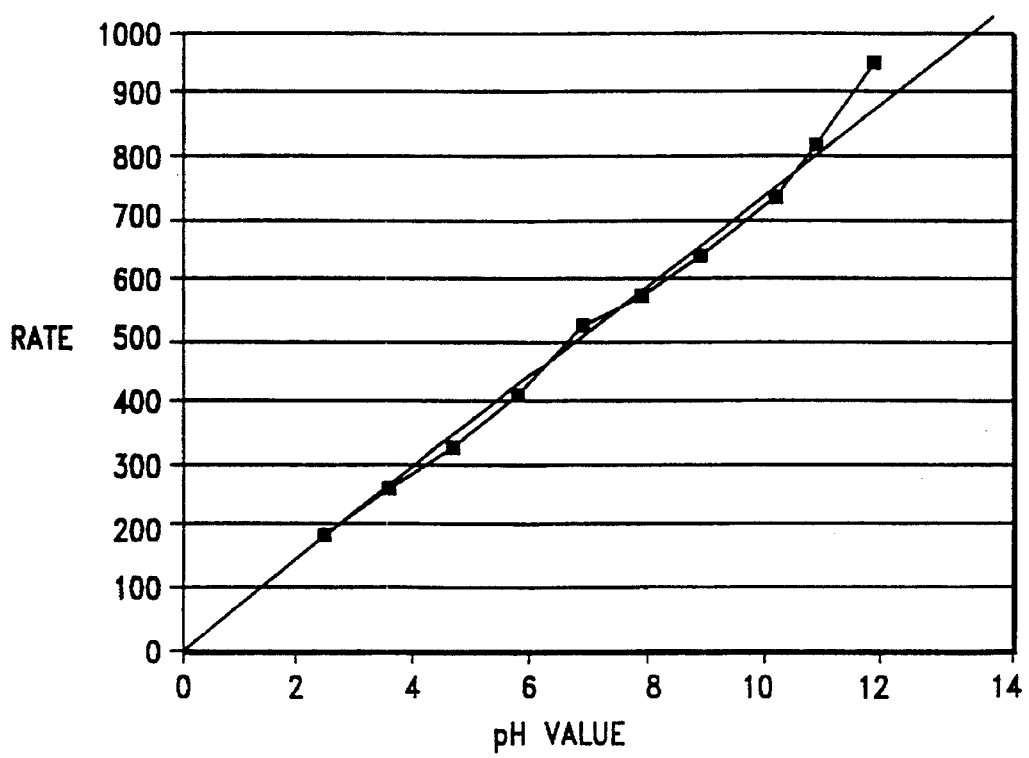
FIG. 2 is a graph depicting the relationship between rate of G6PDH activity (ordinate) and the pH value of a series of standard pH calibrant solutions (abscissa), determined in accordance with the present method.

Relationship Between Glucose-6-Phosphate Dehydrogenase (G6PDH) Enzymatic Rate and pH of the Specimen A series of pH solutions, each solution having a respective pH of 2, 3, 4, 5, 6, 7, 8, 9, 10, 11 or 12, was prepared. Twenty (20) μL of each of the pH solutions was mixed with (a) 125 μL of an enzyme solution containing 1 μg/mL glucose-6-phosphate dehydrogenase (G6PDH) in 50 mM Tris buffer at pH 6.5 and (b) 125 μL of a substrate solution containing 8 mM glucose-6-phosphate (G6P) and 5 mM of nicotinamide adenine dinucleotide (NAD) in 1 mM Tris buffer at pH 5.2. The enzymatic rate of each solution was determined at 37 °C. using a Hitachi 717 clinical chemistry analyzer. A linear relationship between the G6PDH enzyme activity and the pH of the solution was observed (see FIG. 2).

Example 2

Correlation of pH Measured by a pH Meter with pH Measured by the Present Enzymatic Method Twenty (20) μL of each of two calibrator solutions (one having a pH of 2 and the other a pH of 10) were individually mixed with 125 μL of the enzyme solution and 125 μL of the substrate solution of Example 1. The enzymatic activities were measured as described in Example 1, and were subsequently used to establish a calibration curve.

Urine specimens having pH values ranging from pH 2 to pH 12 were prepared. Twenty (20) μL of each urine specimen was individually mixed with 125 μL of the enzyme solution and 125 μL of the substrate solution of Example 1. The enzymatic activities were measured as described in Example 1, and the pH of each urine specimen was determined by extrapolation from the calibration curve of the experimentally determined enzymatic activity to the corresponding pH.

Figure 3:
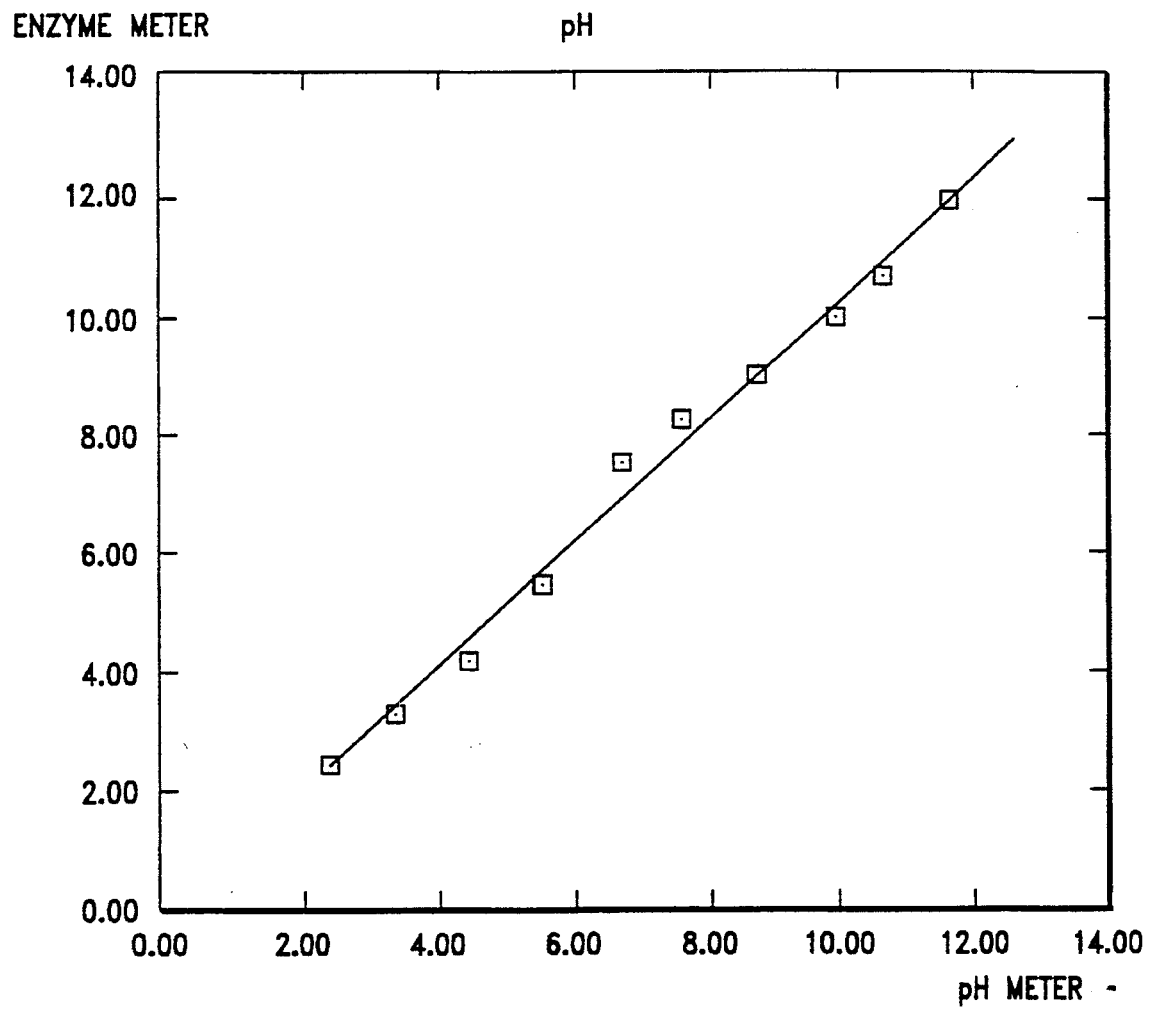
FIG. 3 is a graph depicting the relationship between the pH of sample solutions as determined by present method (ordinate) with the pH of the same sample solutions measured directly with a pH meter, in accordance with the experiment of Example 2 below.

The pH of each urine specimen was independently measured at room temperature with a Corning Model 240 pH meter. An excellent correlation with a regression equation of y (enzyme method)=1.0×(pH meter method) +0.001, and a correlation coefficient (r) of 0.999 was obtained (see FIG. 3).

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by letters patent of the United States is:

1. A method of enzymatically determining the pH of a specimen, comprising
   (a) mixing in a buffered solution (i) a sample of said specimen with (ii) an enzyme having an activity and (iii) a one or more substrates for said enzyme, said buffered solution having a pH effective to provide a direct proportional relationship between said activity of said enzyme and the pH of said specimen, wherein each of said sample, said enzyme, said substrate and said buffered solution is present in an amount effective to provide said direct proportional relationship between said activity of said enzyme and the pH of said specimen,
   (b) determining said activity of said enzyme, and
   (c) correlating said activity of said enzyme to the pH of the specimen.

2. The method of claim 1, wherein said mixing comprises adding said buffered solution to said sample of said specimen to provide a diluted sample, then adding said diluted sample to a mixture of said enzyme and said substrate(s).

3. The method of claim 1, wherein said mixing comprises adding said sample to said enzyme in said buffered solution, then subsequently adding a solution of said substrate(s) thereto.

4. The method of claim 1, wherein said enzyme is selected from the group consisting of glucose-6-phosphate dehydrogenase, cholesterol oxidase, β-galactosidase, glucose oxidase, horseradish peroxidase, uricase and urease.

5. The method of claim 4, wherein said enzyme is glucose-6-phosphate dehydrogenase and said substrate(s) are glucose-6-phosphate and nicotinamide adenine dinucleotide.

6. The method of claim 5, wherein said buffered solution comprises 30–100 mM TRIS-HCl and said pH of said buffered solution is about 6.5.

7. The method of claim 4, wherein said enzyme is glucose oxidase, said substrate is glucose, and said pH is in a range selected from the group consisting of 3.0–4.5 and 7.0–10.0.

8. The method of claim 4, wherein said enzyme is cholesterol oxidase, said substrate is cholesterol, and said pH is in a range selected from the group consisting of 4.0–6.0 and 7.0–9.0.

9. The method of claim 4, wherein said enzyme is β-galactosidase, said substrate is a β-galactoside, and said pH is in a range selected from the group consisting of 5.0–6.5 and 7.5–9.5.

10. The method of claim 4, wherein said enzyme is horseradish peroxidase, said substrates include a donor compound oxidizable by said horseradish peroxidase, and said pH is in a range selected from the group consisting of 4.0–6.0 and 6.8–8.0.

11. The method of claim 4, wherein said enzyme is uricase, said substrate is uric acid, and said pH is in a range selected from the group consisting of 6.0–8.0 and 9.0–11.0.

12. The method of claim 4, wherein said enzyme is urease, said substrate is urea, and said pH is in a range selected from the group consisting of 4.0–6.0 and 6.0–10.0.

13. The method of claim 1, wherein said buffered solution comprises 30–100 mM TRIS-HCl and said pH of said buffered solution is about 6.5.

14. The method of claim 1, wherein said direct proportional relationship is a linear relationship.

15. The method of claim 1, further comprising the step of selecting the pH of said buffered solution such that said pH falls within a range of from a to b, where b is the higher endpoint of the range, a is the lower endpoint of the range, and the activity of said enzyme is roughly linearly proportional to said pH within said range.

16. The method of claim 1, further comprising the steps of calibrating said pH of said buffered solution and said amounts of each of said sample, said enzyme, said substrate(s) and said buffered solution by mixing said buffered solution, said enzyme and said substrate(s) independently with a plurality of specimens each having a known pH, and determining the activity of said enzyme for each of said specimens having a known pH, prior to conducting the method of claim 1.

17. The method of claim 16, wherein said plurality of specimens each having a known pH comprises at least three solutions having a known pH in the range of from 2 to 12.

18. The method of claim 17, wherein said plurality of specimens each having a known pH comprises at least five solutions having a known pH in the range of from 2 to 12.

19. The method of claim 16, wherein each determining step is conducted in a clinical chemistry analyzer.

20. The method of claim 1, wherein said determining step is conducted in a clinical chemistry analyzer.

21. The method of claim 1, wherein said buffered solution also has a buffering capacity effective to provide a direct proportional relationship between said activity of said enzyme and the pH of said specimen.

22. A kit for enzymatically determining the pH of a specimen, comprising (a) an enzyme having an activity, (b) one or more substrates for said enzyme, said substrate(s) being present in an amount effective to determine said activity, and (c) a buffered solution having a pH effective to provide a direct proportional relationship between said activity of said enzyme and the pH of said specimen, wherein each of said enzyme, said substrate and said buffered solution is present in an amount effective to provide said direct proportional relationship between said activity of said enzyme and the pH of said specimen.

23. The kit of claim 22, wherein said effective amount of said buffered solution is relative to an amount of from 5 to 100 µl of said specimen.

24. The kit of claim 22, wherein said direct proportional relationship is a linear relationship.

25. The kit of claim 22, further comprising a reference chart which correlates said enzymatic activity to the pH of said specimen.

26. The kit of claim 22, wherein said kit comprises:

a solution of glucose-6-phosphate dehydrogenase in a TRIS-HCl buffer, and a solution of glucose-6-phosphate and either (i) nicotinamide adenine dinucleotide or (ii) nicotinamide adenine dinucleotide phosphate in a TRIS-HCl buffer.

27. The kit of claim 22, wherein said buffered solution also has a buffering capacity effective to provide a direct proportional relationship between said activity of said enzyme and the pH of said specimen.

* * * * *